United States Patent [19]

Nelson

[11] 4,292,256

[45] * Sep. 29, 1981

[54] N-[(PHOSPHINYL)AMINO]THIO- AND N-[(PHOSPHINOTHIOYL)AMINO]THIOMETHYLCARBAMATES

[75] Inventor: Stephen J. Nelson, Comstock Township, Kalamazoo County, Mich.

[73] Assignee: The Upjohn Company, Kalamazoo, Mich.

[ * ] Notice: The portion of the term of this patent subsequent to Jun. 17, 1997, has been disclaimed.

[21] Appl. No.: 115,474

[22] Filed: Jan. 25, 1980

Related U.S. Application Data

[63] Continuation-in-part of Ser. No. 962,266, Nov. 20, 1978, Pat. No. 4,208,409, which is a continuation-in-part of Ser. No. 874,959, Feb. 3, 1978, abandoned, which is a continuation-in-part of Ser. No. 765,807, Feb. 4, 1977, Pat. No. 4,081,536.

[51] Int. Cl.$^3$ .................. C07F 9/15; A01N 57/26; C07D 339/06

[52] U.S. Cl. .................. 260/937; 424/209; 260/346.22; 549/7

[58] Field of Search .......................... 260/937

[56] References Cited

U.S. PATENT DOCUMENTS 3,932,403  1/1976  Ashton et al. .................. 260/937

*Primary Examiner*—Anton H. Sutto
*Attorney, Agent, or Firm*—Sidney B. Williams, Jr.

[57] ABSTRACT

New phosphinic acid derivatives of aminothio methylcarbamates. The new compounds are active against insects, mites and nematodes.

7 Claims, No Drawings

N-[(PHOSPHINYL)AMINO]THIO- AND N-[(PHOSPHINOTHIOYL)AMINO]THIOMETHYLCARBAMATES

CROSS-REFERENCES TO RELATED APPLICATIONS

This application is a continuation-in-part of application Ser. No. 962,266, filed Nov. 20, 1978, now U.S. Pat. No. 4,208,409, which is a continuation-in-part of application Ser. No. 874,959, filed Feb. 3, 1978, now abandoned, which is a continuation-in-part of application Ser. No. 765,807, filed Feb. 4, 1977 and now U.S. Pat. No. 4,081,536.

The present invention relates to N-[(phosphinyl)amino]thio- and N-[(phosphinothioyl)amino]thio- methylcarbamate pesticides, the essential material constituting a disclosure of which is incorporated here by reference from application Ser. No. 962,266, filed Nov. 20, 1978.

The following described preparations of compounds represent additional exemplification of Applicant's N-[(phosphinyl)amino]thio and N-[(phosphinothioyl)amino]thio- methylcarbamates.

EXAMPLE 1

Methyl N-[[[[[(1,1-dimethylethyl)(5,5-dimethyl-2-oxo-1,3,2-dioxaphosphorinan-2-yl)amino]thio]methylamino]carbonyl]oxy]ethanimidothiate

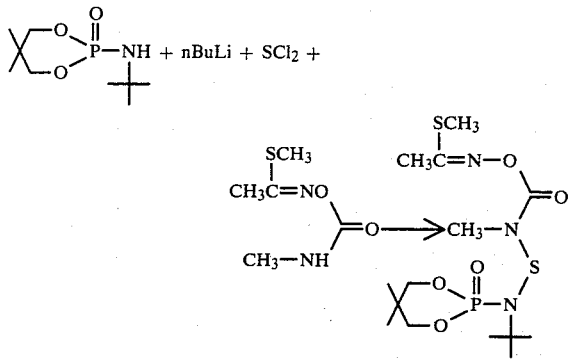

To a slurry of N-(5,5-dimethyl-2-oxo-1,3,2-dioxaphosphorinan-2-yl)-1,1-dimethylethanamine (15.7 g., 70.8 mmoles) in tetrahydrofuran (50 ml.) at −5° is added over a ten minute period a solution of n-butyl lithium in hexane (46 ml. of 1.6 M; 74 mmoles) with rapid stirring under dry nitrogen. This is stirred for 60 minutes at −5° and then transferred under dry nitrogen to an addition funnel and added over a 30 minute period to a solution of freshly distilled sulfur dichloride in tetrahydrofuran (25 ml.) at −5° with stirring. Stirring is continued for two hours at −5° and then filtered under dry nitrogen. The filter cake is washed with tetrahydrofuran (50 ml.) and the filtrates combined and concentrated in vacuo at ≦35°. The residue is redissolved in tetrahydrofuran (75 ml.), cooled to −5°, solid cuprous chloride (0.3 g.) added at once followed immediately by the addition of a solution of methomyl (11.5 g.; 70.8 mmoles) and triethylamine (9.8 ml., 70.8 mmoles) with stirring under dry nitrogen. About four minutes are required. Stirring is continued for two hours at −5°. The reaction mixture is then concentrated in vacuo at ≦45° and the residue taken up in methylene chloride (500 ml.) and washed with ice-water (2×300 ml.). The organic phase is vacuum filtered through celite and dried (anhydrous sodium sulfate). It is then concentrated in vacuo at ≦45° giving 28 g. of viscous oil. Preliminary absorption chromatography on silica gel using 2:1 ethyl acetate:Skellysolve B gives 15 g. of yellow oil. Chromatography of this material on silica gel using 1:4 isopropanol:Skellysolve B gives 4.4 g. (15% yld) as a white crystalline solid; MP 133.5°–134.5° (recrystallized from ethylacetate).

Analysis: Calc'd. for $C_{14}H_{28}N_3O_5PS_2$: C, 40.67; H, 6.83; N, 10.16. Found: C, 40.48; H, 7.04; N, 9.95.

EXAMPLE 2

Methyl N-[[[methyl[[(1-methylethyl)(2-oxo-1,3,2-dioxaphosphorinan-2-yl)amino]thio]amino]carbonyl]oxy]ethanimidothioate

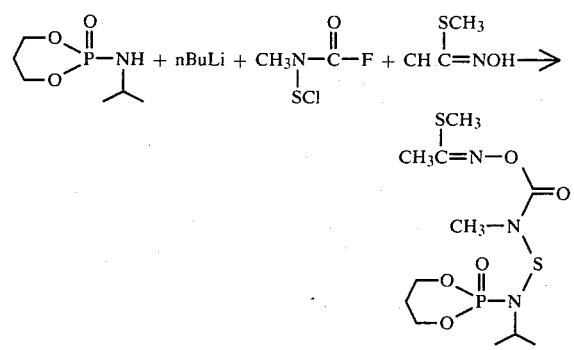

To a solution of N-(1-methylethyl)-2-oxo-1,3,2-dioxaphosphorinan-2-amine (12.7 g.; 70.8 mmoles) in tetrahydrofuran (50 ml.) is added n-butyl lithium in n-hexane (46 ml. of 1.6 M; 74 mmoles) with stirring under dry nitrogen at 0° over a ten minute period. Stirring is continued at 0° to 25° for two hours. The reaction mixture is transferred under dry nitrogen to an addition funnel and added dropwise to a solution of N-chlorothio-N-methylcarbamic fluoride (10.2 g.; 70.8 mmoles) in tetrahydrofuran (50 ml.) with stirring under dry nitrogen at −5°. Approximately ten minutes are required. Stirring is continued for two hours at 0° to 25°. The reaction mixture is cooled to 0° and solid methyl N-hydroxy ethanimidothioate (7.45 g.; 70.8 mmoles) added at once under nitrogen with rapid stirring. This is followed immediately by the dropwise addition of triethylamine (9.8 ml.; 70.8 mmoles) over a period of ten minutes. The reaction mixture is stirred at 0° to 25° under dry nitrogen overnight. It is then gravity filtered and the filtrate concentrated in vacuo giving 25 g. of dark brown oil. This is subjected to absorption chromatography on silica gel; this is eluted stepwise with 70% ethylacetate in Skellysolve B, 100% ethylacetate, and finally 100% acetone giving 10/8 g. of brown crystalline solid. Silica gel chromatography on this material in which 50% acetone in Skellysolve B is the eluant gives 1.98 g. (7.5% yield) of a white crystalline solid; M.P. 134°–135° after recrystallization from ethylacetate.

Analysis: Calc'd. for $C_{11}H_{22}N_3O_5PS_2$: C, 35.57; H, 5.97; N, 11.31. Found: C, 35.61; H, 5.83; N, 11.30.

EXAMPLE 3

Utilizing the procedure of Examples 1 and 2 but substituting the appropriate phosphinic acid amide for N-

(5,5-dimethyl-2-oxo-1,3,2-dioxaphosphorinan-2-yl)-1,1-dimethylethanamine and N-(1-methylethyl)-2-oxo-1,3,2-dioxaphosphorinan-2-amine respectively, the following compounds are prepared.

2-methyl-2-(methylthio)-O-[[[[(5,5-dimethyl-2-thioxo-1,3,2-dioxaphosphorinan-2-yl)(1-methylethyl)amino]thio]methylamino]carbonyl]propanal oxime, m.p. 114° C.(d)

Analysis: Calc'd. for $C_{15}H_{30}N_3O_4PS_3$: C, 40.62; H, 6.82; N, 9.47; S, 21.68. Found: C, 40.14; H, 7.42; N, 9.40; S, 23.50.

O-[[[[(5,5-dimethyl-2-thioxo-1,3,2-dioxaphosphorinan-2-yl)(1-methylethyl)amino]thio]methylamino]carbonyl]-1,3-dithiolan-2-one oxime, m.p. 134°–135.5°.

Analysis: Calc'd. for $C_{13}H_{24}N_3O_4PS_4$: C, 35.04; H, 5.43; N, 9.43; S, 28.78. Found: C, 35.14; H, 5.53; N, 9.46; S, 30.04.

N-cyclohexyl-N-[[[[(1,3-dithiolan-2-ylideneamino)oxy]carbonyl]methylamino]thio]-5,5-dimethyl-1,3,2-dioxaphosphorinan-2-amine-2-sulfide, m.p. 146°–147.5°.

Analysis: Calc'd. for $C_{16}H_{28}N_3O_4PS_4$: C, 39.57; H, 5.81; N, 8.65; S, 26.41. Found: C, 39.88; H, 6.17; N, 8.72; S, 28.90.

Syn and anti-O-[[[[cyclohexyl(5,5-dimethyl-2-thioxo-1,3,2-dioxaphosphorinan-2-yl)amino]thio]methylamino]carbonyl]-2-methyl-2-(methylthio)propanal oxime, m.p. 108°–115° C.

Analysis: Calc'd. for $C_{18}H_{34}N_3O_4PS_3$: C, 44.70; H, 7.09; N, 8.69. Found: C, 44.61; H, 7.38; N, 9.04.

Methyl N-[[[[cyclohexyl(5,5-dimethyl-2-oxo-1,3,2-phosphorinan-2-yl)amino]thio]methylamino]carbonyl]oxy]ethanimidothioate, m.p. 145°.

Analysis: Calc'd. for $C_{16}H_{30}N_3O_5PS_2$: C, 43.72; H, 6.88; N, 9.56. Found: C, 43.35; H, 6.87; N, 9.00.

2,3-dihydro-2,2-dimethyl-7-benzofuronylmethyl[[(1-methylethyl)(2-thioxo-1,3,2-dioxaphosphorinan-2-yl)amino]thio]carbamate, as an oil.

Analysis: Calc'd. for $C_{18}H_{27}N_2O_5PS_2$: C, 48.42; H, 6.10; N, 6.27. Found: C, 48.48; H, 6.86; N, 6.16.

3-(1,1-dimethylethyl)phenyl methyl[[(1-methylethyl)(2-thioxo-1,3,2-dioxaphosphorinan-2-yl)amino]thio]carbamate, as an oil.

Analysis: Calc'd. for $C_{18}H_{29}N_2O_4PS_2$: C, 49.98; H, 6.76; N, 6.48. Found: C, 50.27; H, 6.93; N, 6.25.

2-chloro-3,4-dimethylphenyl methyl[[cyclohexyl(5,5-dimethyl-2-thioxo-1,3,2-dioxaphosphorinan-2-yl)amino]thio]carbamate, m.p. 147°–148° C.

Analysis: Calc'd. for $C_{21}H_{32}ClN_2O_4PS_2$: C, 49.74; H, 6.36; N, 5.52. Found: C, 50.03; H, 6.54; N, 5.46.

Methyl N-[[[[[(3,4-dimethylphenyl)(5,5-dimethyl-2-oxo-1,3,2-dioxaphosphorinan-2-yl)amino]thio]methylamino]carbonyl]oxyethanimidothioate, m.p. 120°–122° C.

Analysis: Calc'd. for $C_{18}H_{28}N_3O_5PS_2$: C, 46.84; H, 6.12; N, 9.10. Found: C, 46.52; H, 6.40; N, 8.91.

Methyl N-[[[methyl[[(benzyl)(2-thioxo-1,3,2-dioxaphosphorinan-2-yl)amino]thio]amino]carbonyl]oxy]ethanimidothioate, as an oil.

Analysis: Calc'd. for $C_{15}H_{22}N_3O_4PS_3$: C, 41.37; H, 5.09; N, 9.65. Found: C, 41.45; H, 4.89; N, 9.61.

I claim:

1. 2-methyl-2-(methylthio)-O-[[[[(5,5-dimethyl-2-thioxo-1,3,2-dioxaphosphorinan-2-yl)(1-methylethyl)amino]methylamino]carbonyl]propanal oxime.

2. Syn and anti-O-[[[[cyclohexyl(5,5-dimethyl-2-thioxo-1,3,2-dioxaphosphorinan-2-yl)amino]thio]methylamino]carbonyl]-2-methyl-2-(methylthio)propanal oxime, m.p. 108°–115° C.

3. Methyl N-[[[[[cyclohexyl(5,5-dimethyl-2-oxo-1,3,2-phosphorinan-2-yl)amino]thio]methylamino]carbonyl]oxyethanimidothioate.

4. Methyl N-[[[methyl[[(1-methylethyl)2-oxo-1,3,2-dioxaphosphorinan-2-yl)amino]thio]amino]carbonyl]oxy]ethanimidothioate.

5. Methyl N-[[[[[(1,1-dimethylethyl)(5,5-dimethyl-2-oxo-1,3,2-dioxaphosphorinan-2-yl)amino]thio]methylamino]carbonyl]oxy]ethanimidothioate.

6. Methyl N-[[[[[(3,4-dimethylphenyl)(5,5-dimethyl-2-oxo-1,3,2-dioxaphosphorinan-2-yl)amino]thio]methylamino]carbonyl]oxy]ethanimidothioate.

7. Methyl N-[[[methyl[[(benzyl)(2-thioxo-1,3,2-dioxaphosphorinan-2-yl)amino]thio]amino]carbonyl]oxy]ethanimidothioate.

* * * * *

UNITED STATES PATENT AND TRADEMARK OFFICE
CERTIFICATE OF CORRECTION

PATENT NO. : 4,292,256
DATED : September 29, 1981
INVENTOR(S) : Stephen J. Nelson It is certified that error appears in the above—identified patent and that said Letters Patent is hereby corrected as shown below:

Column 1, line 2, in the Title: should read -- N[(PHOSPHINOTHIOYL)AMINO]-THIO- METHYLCARBAMATES --.

Column 4, Claim 1, line 25: should read -- )amino]thio]methylamino]-carbonyl]propanal oxime --.

Signed and Sealed this

Twelfth Day of October 1982

[SEAL]

Attest:

GERALD J. MOSSINGHOFF

Attesting Officer    Commissioner of Patents and Trademarks